US009980751B2

(12) United States Patent
Arnin

(10) Patent No.: US 9,980,751 B2
(45) Date of Patent: May 29, 2018

(54) RATCHETED SPINAL DEVICES

(71) Applicant: APIFIX LTD., Carmiel (IL)

(72) Inventor: Uri Arnin, Kiryat Tivon (IL)

(73) Assignee: Apifix Ltd., Carmiel (IL)

( * ) Notice: Subject to any disclaimer, the term of this patent is extended or adjusted under 35 U.S.C. 154(b) by 0 days. days.

(21) Appl. No.: 15/394,855

(22) Filed: Dec. 30, 2016

(65) Prior Publication Data
US 2017/0105765 A1    Apr. 20, 2017

Related U.S. Application Data

(63) Continuation of application No. 14/370,963, filed on Jul. 8, 2014, now abandoned.

(51) Int. Cl.
*A61B 17/70* (2006.01)
*A61B 17/02* (2006.01)

(52) U.S. Cl.
CPC .......... *A61B 17/7014* (2013.01); *A61B 17/02* (2013.01)

(58) Field of Classification Search
CPC .................................. A61B 17/7014–17/7017

USPC ......................................................... 606/258
See application file for complete search history.

(56) References Cited

U.S. PATENT DOCUMENTS

| | | | | |
|---|---|---|---|---|
| 2009/0306717 | A1* | 12/2009 | Kercher | A61B 17/7011 606/258 |
| 2010/0152734 | A1* | 6/2010 | Mulone | A61B 17/663 606/60 |
| 2011/0270314 | A1* | 11/2011 | Mueller | A61B 17/704 606/264 |
| 2012/0083845 | A1* | 4/2012 | Winslow | A61B 17/7007 606/264 |

* cited by examiner

*Primary Examiner* — Nicholas Plionis
(74) *Attorney, Agent, or Firm* — Dekel Patent Ltd.; David Klein

(57) ABSTRACT

A spinal device including a variable-length member including a ratchet mechanism that has an operative configuration that allows a change in length of the variable-length member in one direction and prevents a change in length of the variable-length member in an opposite direction, wherein the variable-length member includes polyaxial-joint attachment members for attachment to bone, which permit pivoting movement of the attachment members about more than one pivoting axis, characterized by a force applicator operative to adjust or advance the ratchet mechanism.

6 Claims, 4 Drawing Sheets

RATCHETED SPINAL DEVICES

FIELD OF THE INVENTION

The present invention relates generally to spinal implants and prostheses, and particularly to spinal implants having ratchet mechanisms, such as a spinal implant with joints that permit movement in different degrees of freedom, or a spinal implant with a force applicator to control a ratchet mechanism.

BACKGROUND OF THE INVENTION

Scoliosis is a spinal deformity affecting many people. Current surgical treatment involves affixing long fusion rods to the spine by pedicle screws. The rod system is intended to force the deformed spine into a more healthy position. Other spinal disorders which are often treated by fusion include hyperkyphosis and hyperlordosis.

As an alternative to fusion, PCT Patent Application PCT/US2011/035278 of the same inventor describes improved spinal devices that can be lengthened or shortened using a ratchet mechanism. The devices have a variable-length member that can be connected to standard pedicle screws as well as to other spinal rods, using appropriate connectors.

SUMMARY OF THE INVENTION

The present invention seeks to provide further improved spinal devices.

In one embodiment, the spinal device is in the form of a spinal rod (the term rod, or rod assembly, refers to one or more elongate components that together function as a rod and which do not necessarily have a cylindrical shape but can also be bars and other shapes) that can be lengthened or shortened using a ratchet mechanism. The rod is a variable-length member that can be connected to standard pedicle screws as well as to other spinal rods, using appropriate connectors. The variable-length member can also be directly connected to, or be supported by, bony elements of the spine.

In one embodiment of the invention, the device can be set to three different configurations:

a. Ratchet mechanism active and the variable-length member (rod) can change in length (extend or contract) in one direction.

b. Ratchet mechanism not active and the variable-length member can move in opposite directions corresponding to the extending and contracting directions.

c. Locked position, wherein the length of the variable-length member is fixed.

In an embodiment of the invention, the selection of these configurations can be done by rotating an internal element of the assembly. For example, the rotation of the internal element can be done using a worm gear mechanism. The worm gear can be activated by a shaft, through a percutaneous procedure or by an implantable mechanism such as an electric motor, magnet arrangement or other means known to those skilled in the art.

In another embodiment of the present invention, the variable-length member can have two portions with different rigidity. For example, the variable-length member can have a flexible portion (e.g., when the ratchet is built such that the rod can be only shortened) like a flexible cable, a rope, a flexible mechanical joint and other means known to those skilled in the art.

In another embodiment of the invention, useful when the rod is supported directly by bone structure of the spine, the hook holding against the bone can have a second hook to fix it to the optimal position.

BRIEF DESCRIPTION OF DRAWINGS

The present invention will be understood and appreciated more fully from the following detailed description, taken in conjunction with the drawings in which.

DETAILED DESCRIPTION OF EMBODIMENTS

Figure 1:
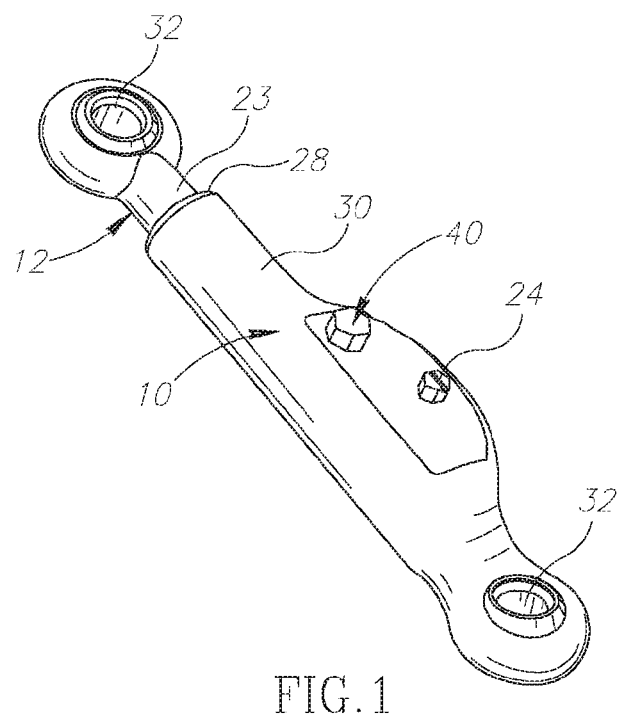
FIG. 1 is a simplified pictorial illustration of a ratcheted spinal device, constructed and operative in accordance with a non-limiting embodiment of the invention.
Figure 2:
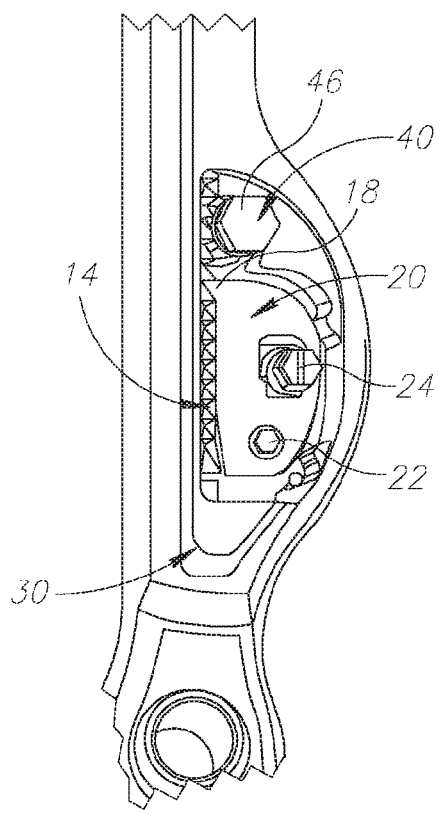
FIG. 2 is a simplified pictorial illustration of a ratchet mechanism of the ratcheted spinal device of FIG. 1.
Figure 3:
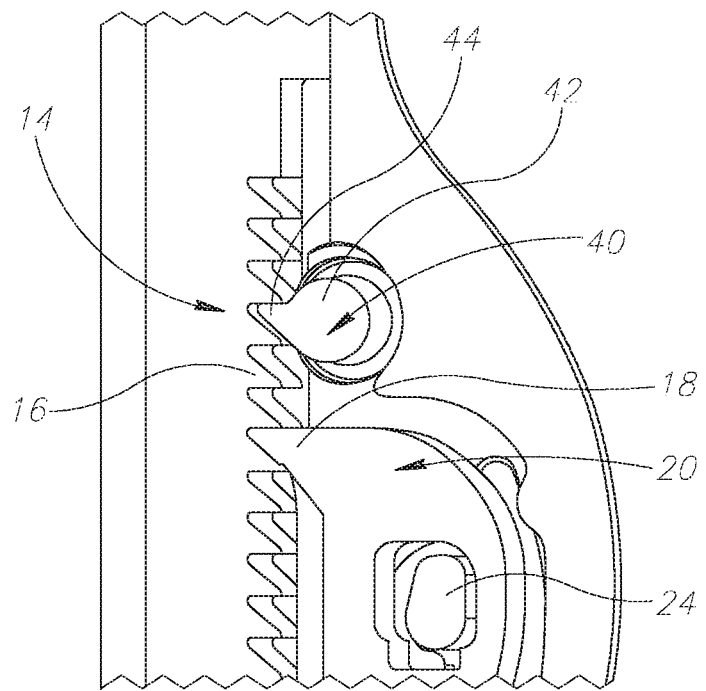
FIG. 3 is a simplified illustration of a force applicator that can adjust or advance the ratchet mechanism of the ratcheted spinal device of FIG. 1.

Reference is now made to FIGS. 1-3, which illustrates a ratcheted spinal device 10, constructed and operative in accordance with another non-limiting embodiment of the invention.

The ratcheted spinal device 10 includes a variable-length member 12. In the illustrated embodiment, the variable-length member 12 is a rod. The term "rod" encompasses any slender element of any size and cross-sectional shape, such as but not limited to, a rod, bar, wire and the like.

As similarly described in PCT Patent Application PCT/US2011/035278, spinal device 10 includes a ratchet mechanism 14 (FIG. 2), which has an operative configuration that allows a change in length of variable-length member 12 in one direction and prevents a change in length of the variable-length member 12 in an opposite direction. Ratchet mechanism 14 has ratchet teeth 16 (FIG. 3; also called ratchet rack 16) formed along an axial portion of variable-length member 12, and a pawl 18 (FIGS. 2-3) arranged to catch on one of the teeth 16. Pawl 18 extends from a controller element 20 (FIG. 2) mounted about a pivot 22 (FIG. 2) and provided with an eccentric cam 24 (FIGS. 2-3). Rotation of eccentric cam 24 moves pawl 18 to one of three positions: a) in ratchet engagement with teeth 16 so that variable-length member 12 can incrementally move in one direction, b) in locked engagement with teeth 16 so that variable-length member 12 cannot move at all, and c) moved out of engagement with teeth 16 so that variable-length member 12 can move in both directions freely.

As seen in FIG. 1, one end 23 of variable-length member 12 is arranged to linearly move through an aperture 28 formed in a housing 30. Variable-length member 12 includes two polyaxial-joint attachment members 32. Both polyaxial-joint attachment members 32 are used to attach device 10 to available bone structure of the spine.

In contradistinction to PCT Patent Application PCT/US2011/035278, in the present invention, spinal device 10 includes a force applicator 40 to control ratchet mechanism 14. Force applicator 40 includes, without limitation, a cam 42 which has a tooth 44 (FIG. 3). The head 46 of cam 42 is shown in FIG. 2 (e.g., hexagonal head); head 46 is not shown for simplicity in FIG. 3. By turning head 46 with a suitable tool, such as a wrench (not shown), in the clockwise direction of FIG. 3, the tooth 44 of cam 42 forcefully moves ratchet rack 16 (upwards in the sense of FIG. 3), so that the tooth in which pawl 18 is engaged moves out of engagement with pawl 18 and the next lower tooth of ratchet rack 16 moves into engagement with pawl 18. Accordingly, force applicator 40 adjusts or advances the ratchet mechanism 14.

Figure 4:
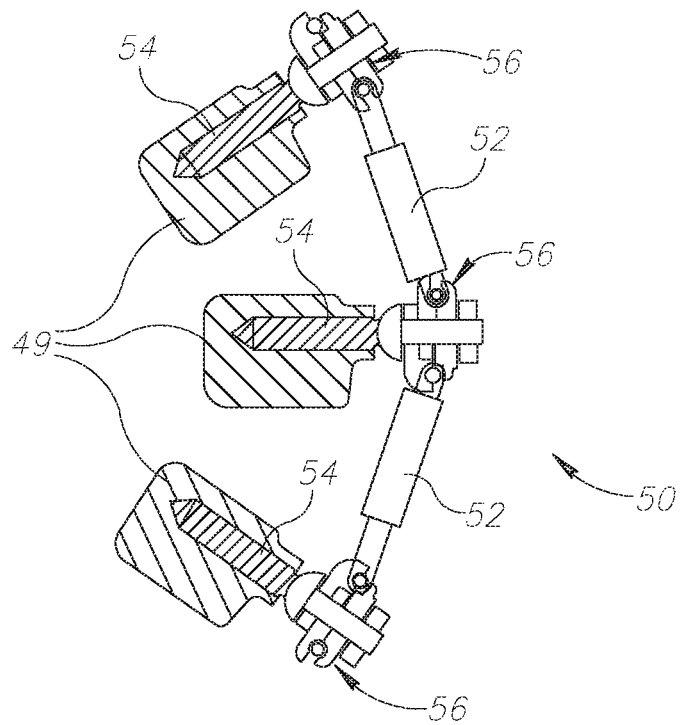
FIG. 4 is a simplified pictorial illustration of a spinal device, including two rod assemblies that are connected between three vertebrae with three bone screws, constructed and operative in accordance with a non-limiting embodiment of the present invention, wherein there are connector assemblies that permit multiple degree-of-freedom movement.

Reference is now made to FIG. 4, which illustrates a spinal device 50, in accordance with an embodiment of the present invention.

In the illustrated embodiment, spinal device 50 includes two rod assemblies 52 that are connected between three vertebrae 49 with three bone screws 54. The rod assemblies 52 may be constructed, without limitation, as ratcheted spinal devices 10 or other spinal devices. Connector assemblies 56 form jointed connections between rod assemblies 52. Connector assemblies 56 permit multiple degree-of-freedom movement of rod assemblies 52 (e.g., variable-length members 12), as will be explained below.

It is noted that any number of vertebrae can be selected, since the design of the system is modular. It is also noted that the middle jointed connection of the two rod assemblies 52 does not have to be connected to any vertebra, meaning one or more vertebrae can be skipped, depending on the application. In the drawing figure, bone screws 54 are inserted in the pedicles, but other insertion locations can be used.

Figure 5:
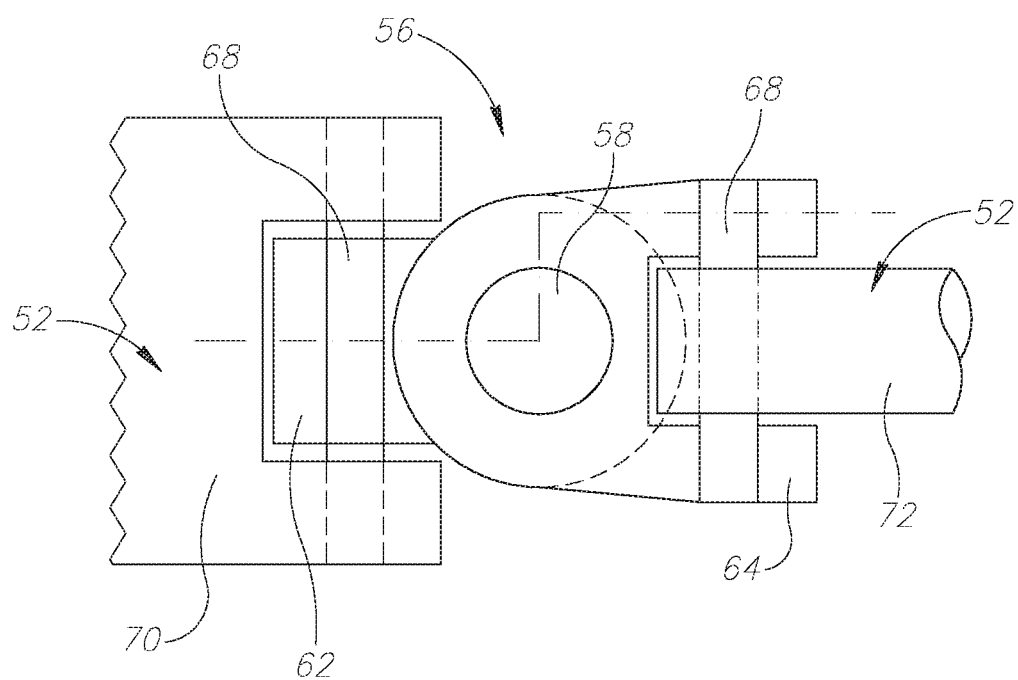
FIG. 5 is a simplified top view illustration of one preferred embodiment of the connector assembly, in accordance with an embodiment of the present invention.
Figure 6A:
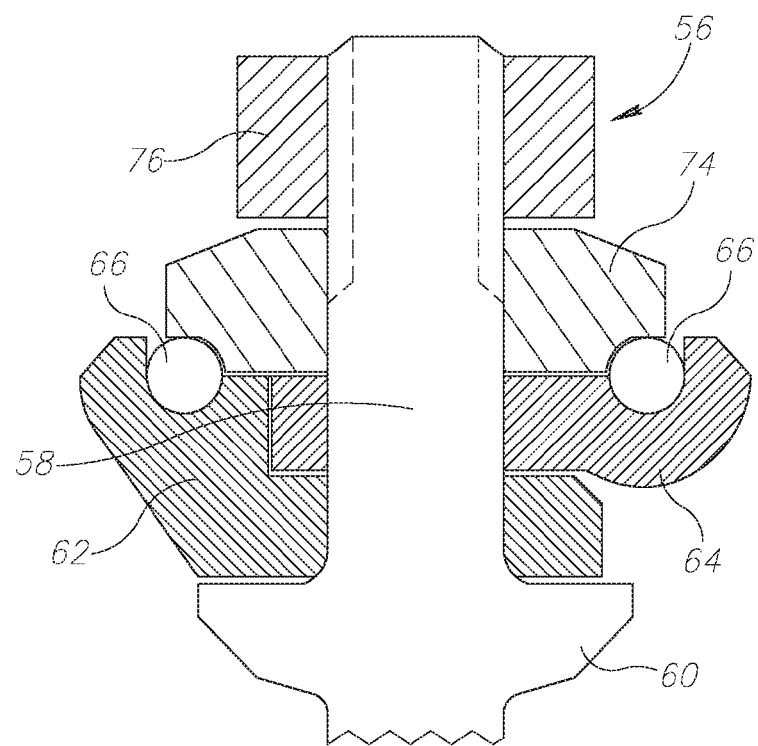
FIG. 6A is a simplified cross-sectional illustration of the embodiment of FIG. 5.

Reference is now made to FIGS. 5 and 6A, which illustrate one preferred embodiment of the connector assembly 56, in accordance with an embodiment of the present invention.

Connector assembly 56 includes a bolt 58 (e.g., a central threaded bolt) having a head 60, and which passes through a hole formed in a first hinge member 62 and a second hinge member 64, which may lie on top of, or be adjacent to, first hinge member 62. Each hinge member is formed with a receiver 66 (FIG. 6A) for receiving therein a pivot pin 68 (FIG. 5). One of the pivot pins 68 is pivotally received in an end 70 of one of the rod assemblies 52, and the other pivot pin 68 is pivotally received in an end 72 of another of the rod assemblies 52 (FIG. 5). Thus adjacent rod assemblies 52 can pivot with respect to one another by means of connector assembly 56. A locking element 74 (such as a nut) secures pins 68 in place (FIG. 6A). Another locking element 76 (such as a nut) is threaded on the end of threaded bolt 58 to complete the assembly (FIG. 6A).

Figure 6B:
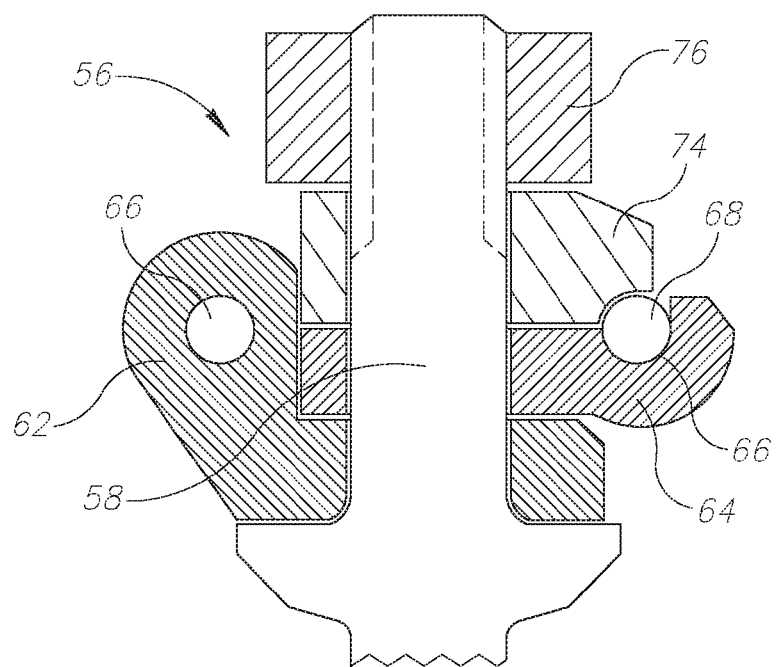
FIG. 6B is a simplified cross-sectional illustration of a modified version of the embodiment of FIG. 5.

FIG. 6B illustrates a variation of the embodiment of FIG. 6A. Like elements are designated by like numerals. The main differences are the shape of locking element 74 and the receiver 66 of the first hinge member 62 has a closed aperture instead of the open aperture of FIG. 6A. Other variations are also possible within the scope of the invention.

Connector assemblies 56 permit multiple degree-of-freedom movement of rod assemblies 52. Rotation is permissible about the longitudinal axis of central threaded bolt 58, and independently about the longitudinal axis of each pin 68, which are perpendicular to the longitudinal axis of central threaded bolt 58.

What is claimed is:

1. A system comprising at least one spinal device, said at least one spinal device comprising:
   a variable-length member comprising a ratchet mechanism that has an operative configuration that allows a change in length of said variable-length member in one direction and prevents a change in length of said variable-length member in an opposite direction, wherein said variable-length member comprises polyaxial-joint attachment members for attachment to bone, which permit pivoting movement of said attachment members about more than one pivoting axis, and
   a force applicator operative to adjust or advance said ratchet mechanism, wherein said force applicator comprises a cam which has a tooth that engages a ratchet rack of said ratchet mechanism, and wherein by turning said cam, said tooth of said cam forcefully moves said ratchet rack so that a tooth of said ratchet rack, in which a pawl of said ratchet mechanism is engaged, moves out of engagement with said pawl and another tooth of said ratchet rack moves into engagement with said pawl.

2. The system according to claim 1, wherein said at least one spinal device comprises a pair of said spinal devices and a connector assembly that forms a jointed connection between said pair of spinal devices that permits multiple degree-of-freedom movement of said pair of spinal devices.

3. The system according to claim 2, further comprising a connector assembly that forms a jointed connection between said variable-length members that permits multiple degree-of-freedom movement of said variable-length members.

4. The system according to claim 3, wherein said connector assembly comprises a bolt which passes through a first hinge member and a second hinge member adjacent said first hinge member, and pivot pins that pivotally connect said spinal devices to said first hinge member and said second hinge member.

5. The system according to claim 4, wherein said connector assembly permits rotation about a longitudinal axis of said bolt, and independently about a longitudinal axis of each pivot pin, which are perpendicular to the longitudinal axis of said bolt.

6. The system according to claim 1, wherein said cam of said force applicator comprises a head configured for turning with a tool.

\* \* \* \* \*